United States Patent
Lee et al.

(10) Patent No.: US 10,669,381 B2
(45) Date of Patent: Jun. 2, 2020

(54) METHOD FOR PREPARING SUPER ABSORBENT POLYMER

(71) Applicant: LG Chem, Ltd., Seoul (KR)

(72) Inventors: Seung Mo Lee, Daejeon (KR); Gi Cheul Kim, Daejeon (KR); Kyu Pal Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/755,296

(22) PCT Filed: Mar. 18, 2016

(86) PCT No.: PCT/KR2016/002777
§ 371 (c)(1),
(2) Date: Feb. 26, 2018

(87) PCT Pub. No.: WO2017/159903
PCT Pub. Date: Sep. 21, 2017

(65) Prior Publication Data
US 2018/0244857 A1    Aug. 30, 2018

(30) Foreign Application Priority Data
Mar. 14, 2016 (KR) .................. 10-2016-0030385

(51) Int. Cl.
| | | |
|---|---|---|
| *B01J 20/26* | (2006.01) | |
| *C08J 3/075* | (2006.01) | |
| *C08J 3/12* | (2006.01) | |
| *C08F 20/06* | (2006.01) | |
| *C08F 2/44* | (2006.01) | |
| *C08F 2/46* | (2006.01) | |
| *C08J 3/24* | (2006.01) | |
| *C08L 33/02* | (2006.01) | |
| *A61L 15/42* | (2006.01) | |
| *A61L 15/60* | (2006.01) | |
| *B01J 20/28* | (2006.01) | |
| *C08J 3/28* | (2006.01) | |

(52) U.S. Cl.
CPC .............. *C08J 3/075* (2013.01); *A61L 15/42* (2013.01); *A61L 15/60* (2013.01); *B01J 20/267* (2013.01); *B01J 20/28047* (2013.01); *C08F 2/44* (2013.01); *C08F 2/46* (2013.01); *C08F 20/06* (2013.01); *C08J 3/12* (2013.01); *C08J 3/24* (2013.01); *C08J 3/245* (2013.01); *C08J 3/28* (2013.01); *C08L 33/02* (2013.01); *B01J 2220/68* (2013.01); *C08J 2333/08* (2013.01)

(58) Field of Classification Search
CPC . C08J 3/075; C08J 3/24; C08J 2333/08; C08J 3/245; C08J 3/28; C08J 3/12; A61L 15/60; A61L 15/42; C08L 33/02; C08F 20/06; C08F 2/44; C08F 2/46; B01J 2220/68; B01J 20/267; B01J 20/28047

USPC ......................................................... 502/402
See application file for complete search history.

(56) References Cited

U.S. PATENT DOCUMENTS

| | | | |
|---|---|---|---|
| 5,118,719 A | 6/1992 | Lind | |
| 5,314,420 A | 5/1994 | Smith et al. | |
| 5,563,218 A | 10/1996 | Rebre et al. | |
| 6,573,330 B1 | 6/2003 | Fujikake et al. | |
| 8,552,071 B1 | 10/2013 | Daniel et al. | |
| 2010/0093949 A1* | 4/2010 | Herfert | ................ A61F 13/53 525/451 |
| 2010/0198177 A1 | 8/2010 | Yahiaoui et al. | |
| 2012/0326071 A1 | 12/2012 | Pasquero et al. | |
| 2013/0037708 A1 | 2/2013 | Matsumoto et al. | |
| 2013/0338328 A1 | 12/2013 | Krauss et al. | |
| 2014/0312273 A1 | 10/2014 | Wattebled et al. | |
| 2014/0371352 A1 | 12/2014 | Dantin et al. | |
| 2015/0259522 A1* | 9/2015 | Lee | .................... B01J 20/261 524/522 |
| 2015/0283284 A1 | 10/2015 | Azad et al. | |
| 2016/0045895 A1 | 2/2016 | Won et al. | |
| 2016/0280866 A1 | 9/2016 | Lee et al. | |
| 2016/0326286 A1 | 11/2016 | Sim et al. | |

FOREIGN PATENT DOCUMENTS

| | | |
|---|---|---|
| CN | 101674856 A | 3/2010 |
| CN | 104144973 A | 11/2014 |
| CN | 104974312 A | 10/2015 |
| EP | 0615736 A1 | 9/1994 |
| EP | 0644211 A1 | 3/1995 |
| EP | 1637105 A1 | 3/2006 |
| EP | 1730218 B1 | 12/2010 |
| EP | 2957576 A1 | 12/2015 |
| EP | 2797566 B1 | 6/2019 |
| JP | 3280077 B2 | 4/2002 |
| JP | 3679146 B2 | 8/2005 |

(Continued)

OTHER PUBLICATIONS

International Search Report for PCT/KR2016/002777 dated Jan. 13, 2017.

(Continued)

*Primary Examiner* — Haytham Soliman
(74) *Attorney, Agent, or Firm* — Lerner, David, Littenberg, Krumholz & Mentlik, LLP

(57) ABSTRACT

The present invention relates to a method for a super absorbent polymer. The method for preparing a super absorbent polymer according to the present invention makes it possible to provide a super absorbent polymer in which characteristics such as a centrifuge retention capacity and an absorption rate are improved in a balanced manner.

9 Claims, No Drawings

(56) References Cited

FOREIGN PATENT DOCUMENTS

| | | |
|---|---|---|
| JP | 2009052009 A | 3/2009 |
| JP | 2009084472 A | 4/2009 |
| JP | 1369060 B2 | 11/2009 |
| JP | 2009280668 A | 12/2009 |
| JP | 2013518961 A | 5/2013 |
| KR | 20000029883 A | 5/2000 |
| KR | 100485227 B1 | 8/2005 |
| KR | 20110118651 A | 10/2011 |
| KR | 20140094536 A | 7/2014 |
| KR | 20140133470 A | 11/2014 |
| KR | 20150032045 A | 3/2015 |
| KR | 20150082098 A | 7/2015 |
| WO | 9806364 A1 | 2/1998 |
| WO | 201207432 A1 | 8/2012 |
| WO | WO-2014077612 A1 * | 5/2014 ............ B01J 20/261 |

OTHER PUBLICATIONS

ESSR for EP Application No. 16894634.1 dated Aug. 3, 2018.
Third Party Observation for Application No. EP16894634.1 dated Jan. 9, 2020.
Bucholz et al., "Modern Superabsorbent Polymer Technology", WILEY-VCH, 1998, pp. 199-201.
Search Report from Chinese Office Action for CN201680052146.8 dated Apr. 7, 2020; 3 pages.

* cited by examiner

METHOD FOR PREPARING SUPER ABSORBENT POLYMER

CROSS-REFERENCE TO RELATED APPLICATION(S)

This application is a national phase entry under 35 U.S.C. § 371 of International Application No. PCT/KR2016/002777, filed Mar. 18, 2016, which claims priority to Korean Patent Application No. 10-2016-0030385, filed Mar. 14, 2016, the disclosures of which are incorporated herein by reference.

TECHNICAL FIELD

The present invention relates to a method for preparing a super absorbent polymer.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like.

The super absorbent polymers started to be practically applied in sanitary products, and now they are widely used for preparation of various products, for example, hygiene products such as diapers for children, water retaining soil products for gardening, water stop materials for the civil engineering, sheets for raising seedling, fresh-keeping agents for food distribution fields, or the like.

In recent years, as the application field increases, the super absorbent polymer requires a variety of physical properties such as an absorbency under pressure (AUP), a permeability, an absorption rate or the like, in addition to the basic absorption characteristics (for example, absorption capacity of a target solution such as water).

However, these absorption characteristics required for the super absorbent polymer have a trade-off relation, and there is a limit in improving these characteristics at the same time. This trade-off relation also applies to changes in physical properties depending on the structure of the super absorbent polymer.

For example, as the structure of the super absorbent polymer is improved in density, the absorbency under pressure can be improved, but the absorption rate decreases due to a decrease in the surface area. Conversely, as the surface area of the super absorbent polymer increases, the absorption rate increases, but the absorption characteristics decreases as a whole.

Accordingly, there is an urgent need for a technique capable of improving the overall absorption properties without sacrificing any of the physical properties required for the super absorbent polymer.

TECHNICAL PROBLEM

It is one object of the present invention to provide a method for preparing a super absorbent polymer in which characteristics such as a centrifuge retention capacity, an absorption rate and the like are improved in a well-balanced manner.

TECHNICAL SOLUTION

According to an embodiment of the invention, there is provided a method for preparing a super absorbent polymer, the method comprising the steps of:

forming a first hydrogel polymer containing a crosslinked polymer of acrylic acid or its salt, and having a first centrifuge retention capacity (CRC; g/g) for a physiological saline solution measured in accordance with EDANA recommended test method No. WSP 241.2 and a first absorption rate (sec) measured according to the vortex test carried out under conditions of stirring 50 ml of 0.9 wt % NaCl solution at a rate of 600 rpm;

forming a second hydrogel polymer containing a crosslinked polymer of acrylic acid or its salt, and having a second centrifuge retention capacity (CRC; g/g) in which a difference between the first centrifuge retention capacity and the second centrifuge retention capacity is −2 g/g to 2 g/g, and a second absorption rate (sec) in which a difference between the first absorption rate and the second absorption rate is 5 sec or more.

forming a mixture of the first hydrogel polymer and the second hydrogel polymer;

drying the polymer mixture;

pulverizing the dried polymer mixture; and surface-crosslinking the pulverized polymer mixture.

Hereinafter, a method for preparing a super absorbent polymer according to a specific embodiment of the present invention will be described in more detail.

The technical terms used in the present specification are only for referring to specific embodiments, and they are not intended to limit the present invention. Further, singular expressions used herein may include plural expressions unless the context clearly indicates otherwise.

In addition, the meaning of the word "comprise", "contain", "include" and the like used in the specification embodies specific characteristics, areas, integers, steps, actions, elements, or components, and does not exclude existence or addition of other specific characteristics, areas, integers, steps, actions, elements, or components.

Further, the terms encompassing ordinal numbers such as first, second, etc. are only used for the purpose of distinguishing one element from another, and these elements are not limited by these terms. For example, a first element could be termed a second element, and, similarly, a second element could be termed a first element without departing from the scope of the present invention.

On the other hand, the present inventors have conducted extensive studies, and found that when a super absorbent polymer is prepared by a method of forming a plurality of hydrogel polymers having mutually different absorption rates while having substantially the same centrifuge retention capacity (CRC), mixing these polymers, and then drying, pulverizing and surface-crosslinking the mixture, it is possible to provide a super absorbent polymer in which characteristics such as a centrifuge retention capacity, an absorption rate and the like, having a trade-off relation therebetween, are improved in a well-balanced manner.

Particularly, it has been found that the super absorbent polymer prepared by the above-mentioned method exhibits a balanced improvement in physical properties as compared with the arithmetic average value of the respective hydrogel polymers used for the preparation thereof and the respective super absorbent polymers formed therefrom.

For example, a super absorbent polymer prepared by mixing a first hydrogel polymer and a second hydrogel polymer having mutually different absorption rates while having substantially the same centrifuge retention capacity, drying, pulverizing and surface-crosslinking the mixture can exhibit more improved absorption rates while having a centrifuge retention capacity equal to or higher than the arithmetic average value of the physical properties of the respective super absorbent polymers formed from the first hydrogel polymer or the second hydrogel polymer.

Furthermore, the physical property-improving effect of the super absorbent polymer according to the above-described preparation method can be achieved by simply physically mixing the super absorbent polymer prepared from the first hydrogel polymer with the super absorbent polymer prepared from the second hydrogel polymer.

According to one embodiment of the invention, there is provided a method for preparing a super absorbent polymer, the method comprising the steps of:

forming a first hydrogel polymer containing a crosslinked polymer of acrylic acid or its salt, and having a first centrifuge retention capacity (CRC; g/g) for a physiological saline solution measured in accordance with EDANA recommended test method No. WSP 241.2, and a first absorption rate (sec) measured according to the vortex test carried out under conditions of stirring 50 ml of 0.9 wt % NaCl solution at a rate of 600 rpm;

forming a second hydrogel polymer containing a crosslinked polymer of acrylic acid or its salt, and having a second centrifuge retention capacity (CRC; g/g) in which a difference between the first centrifuge retention capacity and the second centrifuge retention capacity is −2 g/g to 2 g/g, and a second absorption rate (sec) in which a difference between the first absorption rate and the second absorption rate is 5 sec or more.

forming a mixture of the first hydrogel polymer and the second hydrogel polymer;

drying the polymer mixture;

pulverizing the dried polymer mixture; and surface-crosslinking the pulverized polymer mixture.

In the method for preparing a super absorbent polymer according to an embodiment of the present invention, a plurality of hydrogel polymers having mutually different absorption rates while having substantially the same centrifuge retention capacity (CRC) are used.

Here, the centrifuge retention capacity (CRC) is based on a value which is measured for physiological saline in accordance with EDANA recommended test method No. WSP 241.2; and the absorption rate is based on a value which is measured according to the vortex test carried out under conditions of stirring 50 ml of NaCl solution at a rate of 600 rpm.

According to the embodiment of the present invention, the number of the hydrogel polymers used in the method for preparing the super absorbent polymer is not particularly limited as long as it satisfies the physical properties of the above conditions. For example, as the hydrogel polymers, two or more hydrogel polymers having mutually different absorption rates while having substantially the same centrifuge retention capacity (CRC) may be used. Preferably, as in the one embodiment described above, the first and second hydrogel polymers may be used. The following description is based on the case where two kinds of hydrogel polymers are used. However, it should be apparent to those skilled in the art that this description is not intended to limit the present invention to the use of two hydrogel polymers, and that various modifications may be made by varying the number of polymerization lines applied to the preparation processes.

According to an embodiment of the invention, "the hydrogel polymers having substantially the same centrifuge retention capacity (CRC)" means that a difference in the centrifuge retention capacity between the first hydrogel polymer and the second hydrogel polymer is −2 g/g to 2 g/g, or −1.5 g/g to 1.5 g/g, or −1 g/g to 1 g/g, or −0.5 g/g to 0.5 g/g.

The hydrogel polymers must have mutually different absorption rates while having substantially the same centrifuge retention capacity (CRC). In particular, in order to exhibit the above-mentioned effects according to the embodiment of the invention, it is preferable that the difference in absorption rate between the first and second hydrogel polymers is 5 sec or more, 10 sec or more, or 15 sec or more. However, if the difference in the absorption rate is too large, it may be undesirable because it becomes difficult to control the overall physical properties including the absorption rate of the prepared super absorbent polymer in a balanced manner. Therefore, as a non-limiting example, the difference in absorption rate is 30 sec or less, or 25 sec or less, or 20 sec or less, which can be advantageous for realizing a sufficient effect.

According to an embodiment of the present invention, the step of forming the first hydrogel polymer may include the steps of: polymerizing a monomer aqueous solution containing acrylic acid or its salt in the presence of an internal crosslinking agent to form a first crosslinked polymer; and coarsely pulverizing the first crosslinked polymer.

The step of forming the second hydrogel polymer may include the steps of: polymerizing a monomer aqueous solution containing acrylic acid or its salt in the presence of an internal crosslinking agent to form a second crosslinked polymer; and coarsely pulverizing the second crosslinked polymer.

In the present invention, in order to form the first and second hydrogel polymers having mutually different absorption rates while having substantially the same centrifuge retention capacity (CRC), i) a method of varying the presence/absence of use of the foaming agent during the formation of the hydrogel polymer; or ii) a method of pulverizing the hydrogel polymer so as to have mutually different ranges of sizes during coarse pulverization; or iii) a method of varying the content of an initiator, an internal crosslinking agent, a foaming agent, or an inorganic additive during the formation of the hydrogel polymer; or iv) a method of varying the polymerization conditions such as the temperature of the thermal polymerization or the illuminance of the photo-polymerization during the formation of the hydrogel polymer may be applied.

As an example, in the step of forming the first hydrogel polymer, the monomer aqueous solution further contains a foaming agent; and in the step of forming the second hydrogel polymer, the monomer aqueous solution does not contain a foaming agent, so that the first and second hydrogel polymers satisfying the conditions of physical properties as described above can be formed.

As another example, in the step of coarsely pulverizing the first and second crosslinked polymers, the first crosslinked polymer and the second crosslinked polymer can be pulverized so as to have mutually different ranges of sizes.

As still another example, in the step of forming the first and second crosslinked polymers, the respective monomer aqueous solutions may contain mutually different amounts of polymerization initiators, foaming agents, or inorganic additive, so that the first and second hydrogel polymers satisfying the conditions of physical properties as described above can be formed.

As a further example, in the step of forming the first and second crosslinked polymers, the respective monomer aqueous solutions are polymerized under different temperatures, or polymerized under light irradiation with mutually different illuminance, so that the first and second hydrogel polymers satisfying the conditions of physical properties as described above can be formed.

Hereinafter, the overall contents of each step that can be included in the method for preparing the super absorbent polymer will be described in more detail.

Formation of Hydrogel Polymer

In the method for preparing a super absorbent polymer, a water-soluble ethylenically unsaturated compound or a salt thereof, which had heretofore been known to be usable for the preparation of a super absorbent polymer, may be used as the monomer without any particular limitation.

Specific examples of such monomers may include at least one selected from the group consisting of anionic monomers of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloyl-propanesulfonic acid or 2-(meth)acrylamido-2-methylpropanesulfonic acid, and their salts; non-ionic, hydrophilic group-containing monomers of (meth)acrylamide, N-substituted (meth)acrylate, 2-hydroxyethyl(meth)acrylate, 2-hydroxypropyl(meth)acrylate, methoxypolyethylene glycol (meth)acrylate or polyethylene glycol(meth)acrylate; and amino group-containing unsaturated monomers of (N,N)-dimethylaminoethyl(meth)acrylate or (N,N)-dimethylaminopropyl(meth)acrylamide, and their quaternary product.

Here, the water-soluble ethylenically unsaturated monomer may be those having acidic groups in which at least a part of the acidic group is neutralized. Preferably, the monomers may be those partially neutralized with an alkali substance such as sodium hydroxide, potassium hydroxide, ammonium hydroxide, or the like.

In this case, a degree of neutralization of the monomer may be 40 to 95 mol %, or 40 to 80 mol %, or 45 to 75 mol %. The range of the neutralization degree may vary depending on the final physical properties, but an excessively high degree of neutralization causes the neutralized monomers to be precipitated, and thus polymerization may not readily occur, whereas an excessively low degree of neutralization not only deteriorates the absorbency of the polymer, but also endows the polymer with hard-to-handle properties, such as those of an elastic rubber.

Further, the concentration of the water-soluble ethylenically unsaturated monomer in the monomer composition may be properly controlled in consideration of polymerization time, reaction conditions and the like, and preferably, the concentration may be 20 to 90% by weight, or 40 to 65% by weight. This concentration range may be advantageous for controlling the pulverization efficiency at the time of pulverization of the polymer described below, while preventing the necessity of removing unreacted monomer after polymerization by using a phenomenon of gel effect occurring in the polymerization reaction of the high-concentration aqueous solution. However, if the concentration of the monomer is too low, the yield of the super absorbent polymer may become low. On the contrary, if the concentration of the monomer is too high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

In the preparation method of the embodiment described above, in order to control the porosity of the super absorbent polymer and further improve the absorption rate thereof, a foaming agent can be used together with the monomer.

As the foaming agent, any foaming agent (bubble forming agent) known to be used in the polymerization process of the monomers to allow the formation of a porous polymer may be used. Such a foaming agent may cause bubbles to be generated in the monomer composition so that the polymerized crosslinked polymer exhibits porosity.

Specific examples of the foaming agent may include a carbonate salt of an alkali metal or an alkaline earth metal. More specific examples thereof include sodium bicarbonate, sodium carbonate, potassium bicarbonate, potassium carbonate, calcium bicarbonate, calcium carbonate, magnesium bicarbonate, and magnesium carbonate.

The monomer composition may contain a polymerization initiator generally used in the preparation of a super absorbent polymer.

As a non-limiting example, as the polymerization initiator, a thermal polymerization initiator, a photo-polymerization initiator or the like can be used depending on the polymerization method. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

The photo-polymerization initiator used herein may include, for example, one or more compounds selected from the group consisting of benzoin ether, dialkyl acetophenone, hydroxyl alkylketone, phenyl glyoxylate, benzyl dimethyl ketal, acyl phosphine and α-aminoketone. As the specific example of the acyl phosphine among them, commercially available Lucirin TPO, namely, 2,4,6-trimethyl-benzoyl-trimethyl phosphine oxide, may be used.

The thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4$)$_2S_2O_8$) and the like, Further, examples of the azo-based initiator may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) and the like.

Such polymerization initiator may be added at a concentration of about 0.001 to 1% by weight based on the monomer composition. That is, if the concentration of the polymerization initiator is too low, the polymerization rate becomes low and thus a large amount of residual monomers may be extracted from a final product, which is not preferable. On the contrary, if the concentration of the polymerization initiator is too high, the polymer chains constituting the network becomes short, and thus the content of water-soluble components is increased and physical properties of the polymer may deteriorate, such as a reduction in absorbency under pressure, which is not preferable.

Meanwhile, after the monomer composition containing each of the above-described components is formed in the form of an aqueous solution or suspension, crosslinking polymerization of the monomer composition may proceed in the presence of an internal crosslinking agent to obtain a hydrogel polymer.

As the internal crosslinking agent, any compound can be used as long as it enables introduction of a crosslinking bond during polymerization of the monomer. As a specific example, the internal crosslinking agent may be one or more compounds selected from the group consisting of N,N'-methylenebisacrylamide, trimethylolpropane tri(meth)acrylate, ethylene glycol di(meth)acrylate, polyethylene glycol di(meth)acrylate, propylene glycol di(meth)acrylate, polypropylene glycol di(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, and pentaerythritol tetraacrylate.

The internal crosslinking agent may be added at a concentration of 0.001 to about 5% by weight, about 0.001 to about 3% by weight, about 0.001 to about 1% by weight or about 0.001 to about 0.5% by weight, based on the monomer composition. Particularly, as the internal crosslinking agent is used in an amount of 0.01 to 5 parts by weight, 0.01 to 3 parts by weight, 0.01 to 1 parts by weight, or 0.1 to 0.6 part by weight, relative to 100 parts by weight of the unneutralized water-soluble ethylenically unsaturated compound described above, for example, the unneutralized acrylic acid, the super absorbent polymer having an optimized crosslinked structure and having more excellent physical properties can be produced. If the concentration of the internal crosslinking agent is too low, the absorption rate of the polymer may be lowered and the gel strength may also be weakened, which is not preferable. On the contrary, if the concentration of the internal crosslinking agent is too high, the absorption capacity of the polymer may be lowered, which may not be undesirable as an absorbent.

In addition, the monomer composition may further include an inorganic additive, a thickener, a plasticizer, a preservation stabilizer, an antioxidant and the like, if necessary.

The monomer composition may be in the form of a solution or a dispersed suspension in which the raw materials including the above-mentioned monomers, the polymerization initiator, the internal crosslinking agent, etc. are dissolved in a solvent.

In this case, as the usable solvent, any solvent may be used without limitations in the constitution, as long as it is able to dissolve the above raw materials. Example of the solvent that can be used include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

Meanwhile, formation of the hydrogel polymer through polymerization of the monomer composition may be carried out by a conventional polymerization process, and the process is not particularly limited.

Specifically, the polymerization process is largely classified into thermal polymerization and photo-polymerization according to a polymerization energy source, and the thermal polymerization may be carried out in a reactor like a kneader equipped with stirring spindles and the photo-polymerization may be carried out in a reactor equipped with a movable conveyor belt.

For example, the monomer composition is injected into a reactor like a kneader equipped with the stirring spindles, and thermal polymerization is performed by providing hot air thereto or heating the reactor, thereby obtaining the hydrogel polymer. In this case, the hydrogel polymer may have a size of several centimeters or millimeters when it is discharged from the outlet of the reactor, according to the type of stirring spindles equipped in the reactor. Specifically, the hydrogel polymer may be obtained in various forms according to the concentration of the monomer composition injected thereto, the injection speed, or the like, and a hydrogel polymer having a weight average particle size of 0.1 to 50 mm may be generally obtained.

As another example, when the photo-polymerization of the monomer composition is carried out in a reactor equipped with a movable conveyor belt, the hydrogel polymer may be obtained as a sheet. In this case, the thickness of the sheet may vary according to the concentration of the monomer composition injected thereto and the injection speed, and the polymer sheet is preferably controlled to have a thickness of 0.5 cm to 5 cm in order to secure the production speed while enabling uniform polymerization of the entire sheet.

The hydrogel polymer formed by the above-mentioned method may have a water content of about 40 to 80% by weight. The "water content" as used herein means a weight occupied by moisture with respect to a total amount of the hydrogel polymer. For example, the water content may be the value obtained by subtracting the weight of the dried polymer from the weight of the hydrogel polymer.

Specifically, the water content can be defined as a value calculated by measuring the weight loss due to evaporation of moisture in the polymer in the drying process by raising the temperature of the polymer through infrared heating. At this time, the water content is measured under the drying conditions determined as follows: the drying temperature is increased from room temperature to about 180° C. and then the temperature may be maintained at 180° C., and the total drying time may be set to 20 minutes, including 5 minutes for the temperature rising step.

If necessary, in order to improve the efficiency of the subsequent drying step, a step of pulverizing (so-called "coarsely pulverizing") the hydrogel polymer may be further carried out before drying.

A pulverizing machine that can be used for the coarse pulverization may include a vertical pulverizing device, a turbo cutter, a turbo grinder, a rotary cutter mill, a cutter mill, a disc mill, a shred crusher, a crusher, a chopper, and a disc cutter.

In this case, the coarse pulverization may be carried out so that the particle diameter of the hydrogel polymer becomes 0.1 to 10 mm. That is, in order to increase the drying efficiency, the hydrogel polymer is preferably pulverized to have a particle size of 20 mm or less. However, excessive pulverization may cause agglomeration between particles, and therefore the hydrogel polymer is preferably pulverized to have a particle size of 0.1 mm or more.

When the coarsely pulverizing step is carried out before the drying step of the hydrogel polymer, the polymer may stick to the surface of the pulverizing device because it has a high water content. In order to minimize this phenomenon, steam, water, a surfactant, a fine powder aggregation preventing agent such as clay or silica; a persulfate-based initiator, an azo-based initiator, hydrogen peroxide, and a thermal polymerization initiator such as ascorbic acid, an epoxy-based crosslinking agent, a diol-based crosslinking agent, a crosslinking agent including bifunctional or trifunctional or higher polyfunctional acrylate, or a monofunctional crosslinking agent including a hydroxyl group may be added during the coarse pulverization, if necessary.

Based on the above description, the step of forming the hydrogel polymer according to one embodiment comprises forming the first and second hydrogel polymers having mutually different absorption rates while having substantially the same centrifuge retention capacity (CRC).

Specifically, the step of forming the first hydrogel polymer includes the steps of: polymerizing a monomer aqueous solution containing acrylic acid or its salt in the presence of an internal crosslinking agent to form a first crosslinked polymer; and coarsely pulverizing the first crosslinked polymer.

Further, the step of forming the second hydrogel polymer includes the steps of: polymerizing a monomer aqueous solution containing acrylic acid or its salt in the presence of an internal crosslinking agent to form a second crosslinked polymer; and coarsely pulverizing the second crosslinked polymer.

According to one embodiment, the first and second hydrogel polymers may be prepared using mutually different polymerization lines, respectively. Then, in a subsequent step, a mixture of the first and second hydrogel polymers may be formed, and then subjected to drying, pulverizing and surface crosslinking steps to obtain a super absorbent polymer.

In the present invention, in order to form the first and second hydrogel polymers having mutually different absorption rates while having substantially the same centrifuge retention capacity (CRC), i) a method of varying the presence/absence of use of the foaming agent during the formation of the hydrogel polymer; or ii) a method of pulverizing the hydrogel polymer so as to have mutually different ranges of sizes during coarse pulverization; or iii) a method of varying the content of an initiator, an internal crosslinking agent, a foaming agent, or an inorganic additive during the formation of the hydrogel polymer; or iv) a method of varying the polymerization conditions such as the temperature of the thermal polymerization or the illuminance of the photo-polymerization during the formation of the hydrogel polymer may be applied in the respective polymerization lines.

As an example, in the step of forming the first hydrogel polymer, the monomer aqueous solution further contains a foaming agent; and in the step of forming the second hydrogel polymer, the monomer aqueous solution does not contain a foaming agent, so that the first and second hydrogel polymers satisfying the conditions of physical properties as described above can be formed.

As another example, in the step of coarsely pulverizing the first and second crosslinked polymers, the first crosslinked polymer and the second crosslinked polymer can be pulverized so as to have mutually different ranges of sizes. Specifically, in the coarsely pulverizing step, the first crosslinked polymer may be pulverized so as to have a size of 0.01 to 3 mm, and the second crosslinked polymer may be pulverized so as to have a size of 0.5 to 5 mm.

As still another example, in the step of forming the first and second crosslinked polymers, the respective monomer aqueous solutions may contain mutually different amounts of polymerization initiator, foaming agent, or inorganic additive, so that the first and second hydrogel polymers satisfying the conditions of physical properties as described above can be formed. Specifically, in the step of forming the first crosslinked polymer, the content of the polymerization initiator, the foaming agent or the inorganic additive contained in the monomer aqueous solution can be increased as compared with the step of forming the second crosslinked polymer.

As a further example, in the step of forming the first and second crosslinked polymers, the respective monomer aqueous solutions are polymerized under mutually different temperatures, or polymerized under light irradiation with mutually different illuminance, so that the first and second hydrogel polymers satisfying the conditions of physical properties as described above can be formed. Specifically, in the step of forming the first crosslinked polymer, the polymerization can be carried out under a condition of higher temperature or illuminance than in the step of forming the second crosslinked polymer.

The first and second hydrogel polymers prepared according to the preparation method as described above may have a centrifuge retention capacity (CRC) of 25 g/g or more, or 25 to 50 g/g, preferably 30 to 50 g/g. Also, the difference in centrifuge retention capacity between the first and second hydrogel polymers is −2 g/g to 2 g/g, or −1.5 g/g to 1.5 g/g, or −1 g/g to 1 g/g, or −0.5 g/g to 0.5 g/g, and thus the centrifuge retention capacity of the both polymers may be substantially the same.

The first and second hydrogel polymers must have mutually different absorption rates. In particular, in order to exhibit the above-mentioned effects according to the embodiment of the invention, it is preferable that the difference in absorption rate between the first and second hydrogel polymers is 5 sec or more, 10 sec or more, or 15 sec or more.

However, if the difference in absorption rate is too large, it may be undesirable because it becomes difficult to control the overall physical properties including the absorption rate of the prepared super absorbent polymer in a balanced manner. Therefore, as a non-limiting example, the difference in absorption rate is 30 sec or less, or 25 sec or less, or 20 sec or less, which can be advantageous for realizing a sufficient effect.

Specifically, the first absorption rate of the first hydrogel polymer may be 35 to 50 sec, and the second absorption rate of the second hydrogel polymer may be 45 to 80 sec or 45 to 70 sec.

Further, together with the above-mentioned various physical properties, the first and second hydrogel polymers may have a bulk density of 0.5 to 0.7 g/m, or 0.52 to 0.7 g/ml, or 0.52 to 0.68 g/ml, or 0.52 to 0.65 g/ml.

Formation of Hydrogel Polymer Mixture

The first hydrogel polymer and the second hydrogel polymer prepared by the above-described method are mixed in an appropriate ratio to form a mixture of hydrogel polymers.

According to an embodiment of the invention, the first hydrogel polymer and the second hydrogel polymer are mixed in a weight ratio of 1:99 to 99:1, or 5:95 to 95:5, or 20:80 to 80:20, or 30:70 to 70:30 to form a mixture. Here, the weight ratio of the hydrogel polymers may be adjusted in consideration of physical properties to be imparted to the final super absorbent polymer, and mixing the polymers in the above weight ratio may be advantageous for expressing the above-described effects.

Further, a conventional mixer may be used for forming the mixture.

Drying of the Polymer Mixture

Drying is carried out for a mixture of the hydrogel polymers immediately after polymerization which has been coarsely pulverized or has not undergone the coarsely pulverizing step as described above.

The drying step may be carried out at a temperature of 120 to 250° C., 150 to 200° C., or 160 to 180° C. The above temperature man be defined as a temperature of a heating medium provided for drying, or a temperature inside a drying reactor including the heating medium and the polymer during the drying process.

If the drying temperature is low, and thus the drying time becomes long, the physical properties of the finally formed polymer may be deteriorated. In order to prevent this phenomenon, the drying temperature is preferably 120° C. or higher. In addition, when the drying temperature is higher than necessary, only the surface of the hydrogel polymer is dried, and thus the generation of fine powder may be increased in the pulverizing step to be described later and the physical properties of the finally formed polymer may be deteriorated. In order to prevent this phenomenon, the drying temperature is preferably 250° C. or lower.

The drying time in the drying step is not particularly limited, but can be adjusted to 20 to 90 minutes under the above drying temperature in consideration of the process efficiency and the like.

The drying method in the above drying step can be applied without limitation in the construction as long as it is a method generally used for drying the hydrogel polymer. Specifically, the drying step may be carried out by a method such as hot air supply, infrared irradiation, microwave irradiation or ultraviolet irradiation.

The polymer dried by this method may exhibit a water content of about 0.1 to 10% by weight. That is, when the water content of the polymer is less than 0.1% by weight, excessive drying may cause a rise in the manufacturing cost and a degradation of the crosslinked polymer, which is not advantageous. If the water content of the polymer exceeds 10% by weight, defects may occur in the subsequent step, which is not preferable.

Pulverizing of Dried Polymer Mixture

The pulverizing step is a step for optimizing the surface area of the dried polymer mixture and can be carried out so that the particle size of the pulverized polymer is 150 to 850 μm.

Examples of a pulverizing device that can be used for pulverizing the polymers to have the above particle size may include a pin mill, a hammer mill, a screw mill, a roll mill, a disc mill, a jog mill or the like.

If necessary, in order to control the physical properties of the super absorbent polymer powder finally commercialized, a separate step of classifying particles having a particle diameter of 150 to 850 μm in the polymer powder obtained through the pulverization step may be further carried out.

Surface-crosslinking of the Pulverized Polymer Mixture

The surface crosslinking is a step of increasing the crosslinking density of the surface of the resin particles, and can be carried out by a method of mixing a solution containing a crosslinking agent (so-called "surface crosslinking agent") with the pulverized polymer mixture to perform a crosslinking reaction.

Here, as the surface crosslinking agent, one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride can be used.

According to one embodiment, an epoxy-based surface crosslinking agent may be suitably used in order to obtain better absorption characteristics and the like. Specific examples thereof include polyvalent epoxy-based compounds having two or more epoxy groups per molecule.

Such a polyvalent epoxy-based compound may be, for example, a compound represented by the following Chemical Formula 1:

[Chemical Formula 1]

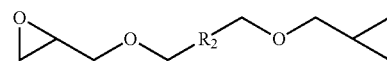

in Chemical Formula 1, $R_2$ is $C_{1-3}$ alkylene.

Further, in the surface crosslinking step, as the surface crosslinking proceeds by adding a multivalent metal cation together with the surface crosslinking agent, the surface crosslinking structure of the super absorbent polymer can be further optimized. This is predicted because these metal cations can further reduce the crosslinking distance by forming a chelate with the carboxyl group (COOH) of the super absorbent polymer.

The content of the surface crosslinking agent may be properly controlled according to the type of the crosslinking agent or reaction conditions, and the content can be preferably adjusted to 0.001 to 5 parts by weight based on 100 parts by weight of the pulverized polymer mixture. If the content of the surface crosslinking agent is too low, surface crosslinking may hardly occur to deteriorate physical properties of the final polymer. On the contrary, if the surface crosslinking agent is used in an excessively large content, the absorption capacity of the resin may be rather low due to excessive surface crosslinking reaction, which is not preferable.

Meanwhile, in order to perform the surface crosslinking, a method of putting a solution containing the surface crosslinking agent (hereinafter referred to as a 'surface crosslinking solution') and the pulverized polymer mixture into a reaction vessel and mixing the same, a method of spraying the surface crosslinking solution on the pulverized polymer mixture, a method of continuously providing the pulverized polymer mixture and the surface crosslinking solution in a continuously operated mixer and mixing them, and the like can be used.

When the surface crosslinking agent is added, a solvent such as water and methanol can be additionally added. The addition of a solvent such as water and methanol can induce more dispersion of the surface crosslinking agent, prevent the aggregation phenomenon of the polymer powder, and further optimize the penetration depth of the surface crosslinking agent. In view of these objects and effects, the content of water to be added may be adjusted to 0.5 to 10 parts by weight based on 100 parts by weight of the pulverized polymer.

The surface crosslinking may be carried out at a temperature of 100 to 250° C., and may be continuously performed after the drying and pulverizing step which is carried out at a relatively high temperature.

Specifically, the conditions of the surface crosslinking step may be the conditions where the maximum reaction temperature is 140° C. or higher, or 160 to 200° C., and the retention time at the maximum reaction temperature is 20 minutes or more, or 20 minutes or more and 1 hour or less. In addition, the temperature raising time required to reach from a temperature at the start of the first reaction, for example, a temperature of about 30° C. or more, or 30 to 120° C. to the maximum reaction temperature can be controlled to about 10 minutes or more, or about 10 minutes or more and 1 hour or less. The surface crosslinking structure is optimized by satisfying the above-mentioned surface cross-linking process conditions, so that a super absorbent polymer exhibiting more excellent absorption characteristics and the like can be produced.

The temperature raising means for the surface crosslinking reaction is not particularly limited. The heating can be carried out by providing a heating medium or directly providing a heating source. The type of heat medium that can be used here includes a heated fluid such as steam, hot air, hot oil, etc., but it is not limited thereto. Further, the temperature of the heating medium to be provided can be appropriately selected in consideration of the means of the heating medium, the temperature raising speed, and the temperature raising target temperature. Meanwhile, a heat source to be provided directly may include a heating method using electricity or a heating method using gas.

The super absorbent polymer obtained according to the preparation method of one embodiment described above can physical properties such as a centrifuge retention capacity and an absorbency under load in a well-balanced manner, and exhibit excellent physical properties that can be suitably used for sanitary articles such as diapers.

Particularly, the super absorbent polymer produced by the above-mentioned method can exhibit more improved absorption rates while having a centrifuge retention capacity equal to or higher than the arithmetic average value of the physical properties of the respective hydrogel polymers used for the preparation thereof and the super absorbent polymer formed therefrom.

According to one embodiment, the super absorbent polymer obtained according to the above-described preparation method may have a centrifuge retention capacity (CRC) for a physiological saline solution of 25 g/g or more, or 25 to 50 g/g, or 30 to 50 g/g, or 35 to 50 g/g, or 36 to 48 g/g, which is measured in accordance with EDANA recommended test method No. WSP 241.2.

Further, the super absorbent polymer may have an absorption rate of 55 sec or less, or 50 sec or less, or 45 sec or less, or 35 to 55 sec, which is measured according to the vortex test carried out under conditions of stirring 50 ml of 0.9 wt % NaCl solution at a rate of 600 rpm.

Further, the super absorbent polymer may have an absorbency under pressure (AUP) for a physiological saline solution of 15 g/g or more, or 15 to 30 g/g, or 20 to 30 g/g, which is measured in accordance with EDANA recommended test method No. WSP 241.2, and a bulk density of 0.5 to 0.7 g/ml.

ADVANTAGEOUS EFFECTS

The method for preparing a super absorbent polymer according to the present invention makes it possible to provide a super absorbent polymer in which characteristics such as a centrifuge retention capacity and an absorption rate are improved in a well-balanced manner.

DETAILED DESCRIPTION OF THE EMBODIMENT

Hereinafter, preferred Examples are provided for better understanding of the present invention. However, these Examples are provided for illustrative purposes only and the invention are not intended to be limited by these Examples.

In the Preparation Examples, Examples, and Comparative Examples described below, the physical properties of the hydrogel polymer and the super absorbent polymer were evaluated by the following methods.

(1) Centrifuge Retention Capacity (CRC)

The centrifuge retention capacity for a physiological saline solution was measured in accordance with EDANA (European Disposables and Nonwovens Association) recommended test method No. WSP 241.3.

Specifically, $W_0(g)$ (about 0.2 g) of the super absorbent polymer was uniformly put in a nonwoven fabric-made bag, followed by sealing. Then, the bag was immersed in a physiological saline solution composed of 0.9 wt % aqueous sodium chloride solution at room temperature. After 30 minutes, water was removed from the bag by centrifugation at 250 G for 3 minutes, and the weight $W_2(g)$ of the bag was then measured. Further, the same procedure was carried out without using the super absorbent polymer, and then the resultant weight $W_1(g)$ was measured.

Using the respective weights thus obtained, CRC (g/g) was determined according to the following Calculation Equation 1.

$$CRC(g/g) = \{[W_2(g) - W_1(g) - W_0(g)]/W_0(g)\}$$ [Calculation Equation 1]

In the above equation 1, $W_0(g)$ is an initial weight(g) of the polymer, $W_1(g)$ is the weight of the device not including the polymer, which is measured after immersing and absorbing the polymer into a physiological saline solution for 30 minutes and then dehydrating the same by using a centrifuge at 250G for 3 minutes, and $W_2(g)$ is the weight of the device including the polymer, which is measured after immersing and absorbing the polymer into a physiological saline solution at room temperature for 30 minutes and then dehydrating the same by using a centrifuge at 250G for 3 minutes.

(2) Absorption Rate (Vortex Time)

50 ml of a 0.9 wt % NaCl solution was put in a 100 ml beaker, and then 2.00 g of a polymer was added thereto while stirring at 600 rpm using a stirrer. Then, the vortex time was calculated by measuring in seconds the amount of time until a vortex of the liquid caused by the stirring disappeared and a smooth surface was formed.

(3) Absorbency Under Pressure (AUP)

The absorbency under pressure was measured in accordance with EDANA (European Disposables and Nonwovens Association) recommended test method No. WSP 242.3.

Specifically, a 400 mesh stainless screen was installed in the bottom of a plastic cylinder having an inner diameter of 60 mm. $W_0(g)$ (about 0.90 g) of a super absorbent polymer were uniformly scattered on the stainless screen under conditions of room temperature and relative humidity of 50%. Then, a piston which could provide a load of 4.83 kPa (0.7 psi) uniformly was designed so that the outer diameter was slightly smaller than 60 mm and thus it could move freely up and down without any gap with the inner wall of the cylinder. At this time, the weight $W_3(g)$ of the device was measured.

A glass filter having a diameter of 90 mm and a thickness of 5 mm was placed in a Petri dish having the diameter of 150 mm, and a physiological saline solution composed of 0.90 wt % sodium hydroxide aqueous solution was poured until the surface level became equal to the upper surface of the glass filter. Then, a sheet of filter paper having a diameter of 90 mm was placed on the glass filter. The measuring device was placed on the filter paper, so that the liquid was absorbed under load for one hour. After one hour, the measuring device was lifted and the weight $Wb(g)$ was measured.

Using each weight thus obtained, AUP (g/g) was calculated according to the following Calculation Equation 2.

$$AUP(g/g) = [W_b - W_a]/W \qquad \text{[Calculation Equation 2]}$$

(4) Bulk Density (BD)

The bulk density was measured in accordance with the EDANA (European Disposables and Nonwovens Association) recommended test method No. WSP 250.3.

For measurement of the bulk density, a cylindrical measuring cup made of stainless steel material (capacity 100.0±0.5 mL, internal diameter 45.0±0.1 mm, internal height 63.1±0.1 mm) and funnel (lower diameter 10.00±0.01 mm, height 145.0±0.5 mm, internal inclination angle 20°) was prepared. The weight $W_1$(g) of an empty measuring cup was measured, and the arranged so that the distance from the top of the measuring cup to the bottom of the funnel was 40.0±2 mm. 100 g of super absorbent polymer was weighted in a state where the bottom of the funnel closed, and added to the funnel. Then, the bottom of the funnel was opened so that the super absorbent polymer was added to the measuring cup. After removing the super absorbent polymer that is stacked above the top of the measuring cup using a paint knife, the weight $W_2$(g) of the measuring cup containing the super absorbent polymer was measured.

Using each weight thus obtained, the bulk density was calculated according to the following Calculation Equation 3.

$$BD\ (g/mL) = \{W_2 - W_1\}/100 \qquad \text{[Calculation Equation 3]}$$

Preparation Example 1

(Preparation of First Hydrogel Polymer)

100 g of acrylic acid, 0.31 g of polyethylene glycol diacrylate (Mw 598) as an internal crosslinking agent, 0.008 g of diphenyl(2,4,6-trimethylbenzoyl)-phosphine oxide as a UV initiator, 123.5 g of 31.5% caustic soda (NaOH), 0.200 g of sodium persulfate, 0.18 g of $NaHCO_3$, 0.008 g of S-1670 as a sucrose stearate type emulsifier, and 38.4 g of water were mixed to prepare a monomer composition having a monomer concentration of 44% by weight.

The monomer composition was introduced through a feeder of a polymerization reactor equipped with a continuously moving conveyor belt. UV polymerization was performed for 2 minutes by irradiating ultraviolet rays (irradiation amount: 2 $mW/cm^2$) through a UV irradiation device to obtain a first hydrogel polymer.

8.9 g of water was further added to the first hydrogel polymer, which was then transferred to a cutter and cut into a size of 0.2 cm. At this time, the water content of the cut hydrogel polymer was 50% by weight.

Preparation Example 2

(Preparation of Second Hydrogel Polymer)

100 g of acrylic acid, 0.23 g of polyethylene glycol diacrylate (Mw 598) as an internal crosslinking agent, 0.008 g of diphenyl(2,4,6-trimethylbenzoyl)-phosphine oxide as a UV initiator, 123.5 g of 31.5% caustic soda (NaOH), 0.200 g of sodium persulfate, and 36.6 g of water were mixed to prepare a monomer composition having a monomer concentration of 47% by weight.

The monomer composition was introduced through a feeder of a polymerization reactor equipped with a continuously moving conveyor belt. UV polymerization was performed for 2 minutes by irradiating ultraviolet rays (irradiation amount: 2 $mW/cm^2$) through a UV irradiation device to obtain a second hydrogel polymer.

8.9 g of water was further added to the second hydrogel polymer, which was then transferred to a cutter and cut into a size of 0.2 cm. At this time, the water content of the cut hydrogel polymer was 50% by weight.

Example 1

(Preparation of Mixture of Hydrogel Polymers)

A mixture in which the first hydrogel polymer according to Preparation Example 1 and the second hydrogel polymer according to Preparation Example 2 were mixed at a weight ratio of 50:50 was prepared.

(Preparation of Super Absorbent Polymer Using the Mixture of Hydrogel Polymers)

The polymer mixture was spread on a stainless steel wire gauze to a thickness of about 30 mm and dried in a hot air oven at 185° C. for 40 minutes. The dried polymer mixture thus obtained was pulverized using a pin mill pulverizing device and classified with a standard mesh sieve according to ASTM standard to obtain a polymer powder having a particle size (average particle diameter) of 150 to 850 µm.

Then, while adding a surface crosslinking solution containing 0.1 g of ethylene glycol diglycidyl ether, 4 g of methanol and 4 g of water to 100 g of the polymer powder, uniform mixing was carried out, and then the mixture was dried in a hot air oven at 140° C. for 30 minutes to obtain a surface-crosslinked super absorbent resin polymer powder.

Comparative Example 1

(Preparation of Super Absorbent Polymer)

The first hydrogel polymer according to Preparation Example 1 was spread on a stainless steel wire gauze to a thickness of about 30 mm and dried in a hot air oven at 185° C. for 40 minutes. The dried polymer mixture thus obtained was pulverized using a pin mill pulverizing device and classified with a standard mesh sieve according to ASTM standard to obtain a polymer powder having a particle size (average particle diameter) of 150 to 850 µm.

Then, while adding a surface crosslinking solution containing 0.1 g of ethylene glycol diglycidyl ether, 4 g of methanol and 4 g of water to 100 g of the polymer powder, uniform mixing was carried out, and then the mixture was dried in a hot air oven at 140° C. for 30 minutes to obtain a surface-crosslinked super absorbent resin polymer powder.

Comparative Example 2

(Preparation of Super Absorbent Polymer)

The second hydrogel polymer according to Preparation Example 2 was spread on a stainless steel wire gauze to a thickness of about 30 mm and dried in a hot air oven at 185° C. for 40 minutes. The dried polymer mixture thus obtained was pulverized using a pin mill pulverizing device and classified with a standard mesh sieve according to ASTM standard to obtain a polymer powder having a particle size (average particle diameter) of 150 to 850 µm.

Then, while adding a surface crosslinking solution containing 0.1 g of ethylene glycol diglycidyl ether, 4 g of methanol and 4 g of water to 100 g of the resin powder, uniform mixing was carried out, and then the mixture was dried in a hot air oven at 140° C. for 30 minutes to obtain a surface-crosslinked super absorbent resin polymer powder.

Test Example 1

The physical properties of the mixture of the hydrogel polymer according to Preparation Examples and the hydrogel polymer used in Examples were measured by the above-mentioned methods. The values are shown in Table 1 below.

TABLE 1

(Physical properties of mixture of hydrogel polymer and hydrogel polymer)

| | Preparation Example | | arithmetic average value | Example 1 (Mixture) |
|---|---|---|---|---|
| | 1 | 2 | | |
| Absorption rate (sec) | 48 | 65 | 56.5 | 52 |
| CRC (g/g) | 44.5 | 44.2 | 44.35 | 44.3 |
| BD (g/ml) | 0.54 | 0.62 | 0.58 | 0.58 |

Test Example 2

The physical properties of the super absorbent polymers according to Examples and Comparative Examples were measured by the above-mentioned methods. The values are shown in Table 2 below.

TABLE 2

(Physical properties of super absorbent polymers)

| | Comparative Example | | arithmetic average value | Example 1 (SAP) |
|---|---|---|---|---|
| | 1 | 2 | | |
| Absorption rate (sec) | 39 | 57 | 48 | 42 |
| CRC (g/g) | 36.5 | 35.1 | 35.8 | 36.2 |
| AUP (g/g) | 21.3 | 22.8 | 22.05 | 23.0 |
| BD (g/ml) | 0.52 | 0.62 | 0.57 | 0.58 |

Referring to the above Tables 1 and 2, it was confirmed that the mixture of the hydrogel polymers and the super absorbent polymers according to Examples exhibited physical properties improved in an equivalent or higher manner as compared with the arithmetic average value of the respective hydrogel polymers (Preparation Examples 1 and 2) used for the preparation thereof and the respective super absorbent polymers (Comparative Examples 1 and 2) formed therefrom.

The invention claimed is:

1. A method for preparing a super absorbent polymer, comprising:
   forming a first hydrogel polymer containing a crosslinked polymer of acrylic acid or its salt, and having a first centrifuge retention capacity (CRC; g/g) for a physiological saline solution measured in accordance with EDANA recommended test method No. WSP 241.2 and a first absorption rate (sec) measured according to the vortex test carried out under conditions of stirring 50 ml of 0.9 wt % NaCl solution at a rate of 600 rpm, wherein the first hydrogel polymer has a size of 0.01 to 3 mm;
   forming a second hydrogel polymer containing a crosslinked polymer of acrylic acid or its salt, and having a second centrifuge retention capacity (CRC; g/g) in which a difference between the first centrifuge retention capacity and the second centrifuge retention capacity is −2 g/g to 2 g/g, and a second absorption rate (sec) in which a difference between the first absorption rate and the second absorption rate is 5 sec or more, wherein the second hydrogel polymer has a size of 0.5 to 5 mm;
   forming a mixture of the first hydrogel polymer and the second hydrogel polymer;
   drying the polymer mixture;
   pulverizing the dried polymer mixture; and
   surface-crosslinking the pulverized polymer mixture,
   wherein the first hydrogel polymer and second hydrogel polymer have a bulk density of 0.5 to 0.7 g/m as measured according to EDANA (European Disposables and Nonwovens Association) WSP 250.3,
   the super absorbent polymer has a centrifuge retention capacity (CRC) for a physiological saline solution of 36 to 50 g/g which is measured in accordance with EDANA recommended test method No. WSP 241.2, and
   wherein the first hydrogel polymer and second hydrogel polymer have a water content of about 40 to 80% by weight.

2. The method of claim 1, wherein
   in the forming the first hydrogel polymer, the monomer aqueous solution further contains a foaming agent; or in the step of coarsely pulverizing the first and second crosslinked polymers, the first crosslinked polymer and the second crosslinked polymer are pulverized so as to have mutually different ranges of sizes.

3. The method of claim 1, wherein
   in the step of forming the first and the second crosslinked polymers, the respective monomer aqueous solutions contain mutually different amounts of polymerization initiators, foaming agents, or inorganic additives.

4. The method of claim 1, wherein
   in the step of forming the first and second crosslinked polymers, the respective monomer aqueous solutions are polymerized under mutually different temperatures, or polymerized under light irradiation with mutually different illuminance.

5. The method of claim 1, wherein the first centrifuge retention capacity and the second centrifuge retention capacity are 25 to 50 g/g, respectively, the first absorption rate is 35 to 50 sec, and the second absorption rate is 45 to 80 sec.

6. The method of claim 1, wherein the surface crosslinking step is carried out in the presence of a polyvalent epoxy-based compound having two or more epoxy groups per molecule, wherein the polyvalent epoxy-based compound is represented by the following Chemical Formula 1:

[Chemical Formula 1]

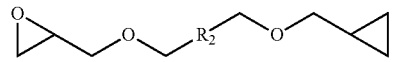

wherein, $R_2$ is $C_{1-3}$ alkylene.

7. The method of claim 1, wherein the super absorbent polymer has an absorption rate of 35 to 55 sec which is measured according to the vortex test carried out under conditions of stirring 50 ml of 0.9 wt % NaCl solution at a rate of 600 rpm; an absorbency under pressure (AUP) for a physiological saline solution of 15 to 30 g/g which is measured in accordance with EDANA recommended test method No. WSP 241.3, and a bulk density of 0.5 to 0.7 g/ml as measured according to EDANA (European Disposables and Nonwovens Association) WSP 250.3.

8. The method of claim 1, wherein the first and second hydrogel polymers are mixed after being formed in mutually different polymerization lines.

9. The method for preparing a super absorbent polymer super absorbent polymer of claim 1, wherein
- the forming the first hydrogel polymer includes: polymerizing a monomer aqueous solution containing acrylic acid or its salt in the presence of an internal crosslinking agent to form a first crosslinked polymer; and coarsely pulverizing the first crosslinked polymer; and
- the forming the second hydrogel polymer includes: polymerizing a monomer aqueous solution containing acrylic acid or its salt in the presence of an internal crosslinking agent to form a second crosslinked polymer; and coarsely pulverizing the second crosslinked polymer.

* * * * *